(12) United States Patent
Ding et al.

(10) Patent No.: US 9,138,717 B2
(45) Date of Patent: Sep. 22, 2015

(54) HIGH-SPEED MIXING REACTOR AND APPLICATION THEREOF

(75) Inventors: Jiansheng Ding, Yantai (CN); Dezhen Sun, Yantai (CN); Weiqi Hua, Yantai (CN); Qingle Hou, Yantai (CN); Wenbo Wang, Yantai (CN); Xueli Yu, Yantai (CN)

(73) Assignee: WANHUA CHEMICAL GROUP CO., LTD, Shandong (CN)

( * ) Notice: Subject to any disclaimer, the term of this patent is extended or adjusted under 35 U.S.C. 154(b) by 59 days.

(21) Appl. No.: 13/499,703

(22) PCT Filed: Dec. 29, 2010

(86) PCT No.: PCT/CN2010/080434
§ 371 (c)(1),
(2), (4) Date: Mar. 18, 2013

(87) PCT Pub. No.: WO2012/088671
PCT Pub. Date: Jul. 5, 2012

(65) Prior Publication Data
US 2013/0178596 A1 Jul. 11, 2013

(51) Int. Cl.
*B01F 15/02* (2006.01)
*B01J 19/18* (2006.01)
(Continued)

(52) U.S. Cl.
CPC ............... *B01J 19/18* (2013.01); *B01F 7/008* (2013.01); *B01F 7/024* (2013.01); *B01F 7/025* (2013.01);
(Continued)

(58) Field of Classification Search
CPC ..................................................... B01J 19/18
USPC .......... 366/169.1, 170.3, 170.4; 422/225–227
See application file for complete search history.

(56) References Cited

U.S. PATENT DOCUMENTS 1,152,769 A * 9/1915 Trent ............................ 422/225
2,392,542 A 1/1946 Matuszak
(Continued)

FOREIGN PATENT DOCUMENTS

CN 1304927 7/2001
CN 101153015 4/2008
(Continued)

OTHER PUBLICATIONS

International Search Report mailed Oct. 13, 2011, in corresponding PCT Application No. PCT/CN2010/080434.
(Continued)

*Primary Examiner* — David Sorkin
*Assistant Examiner* — Abbas Rashid
(74) *Attorney, Agent, or Firm* — Locke Lord LLP; Jeffrey D. Hsi

(57) ABSTRACT

Disclosed is a rapid mixing reactor, comprising a first feed-in passage housing, a reactor housing, a second feed-in passage, a hollow blade-wheel feed distributor, a rotation shaft, and a first feed distributor, wherein the first feed-in passage housing and the reactor housing are constructed coaxially and communicated with each other; the second feed-in passage, the hollow blade-wheel feed distributor and the rotation shaft each are fixed in connection with each other in the sequence along the central axis of the reactor; the hollow blade-wheel feed distributor is located within the reactor housing and rotates axially under the driving force of the rotation shaft; the second feed-in passage is connected with the hollow blade-wheel feed distributor; the first feed-in passage housing is set up with at least one first feed-in inlet therein; the reactor housing is set up with at least one reaction liquid outlet at its distal end; and the first feed distributor and the hollow blade-wheel feed distributor are provided with first feed-in jetting hole(s) and second feed-in jetting hole(s), respectively. The reactor is capable of effecting instantaneously rapid mixing of two streams of fluid under a massive capacity, and improving the yield and quality of the target product.

20 Claims, 6 Drawing Sheets

(51) Int. Cl.
- *B01F 7/00* (2006.01)
- *B01F 7/02* (2006.01)
- *B01J 19/00* (2006.01)
- *B01J 19/26* (2006.01)
- *C07C 209/78* (2006.01)
- *C07C 263/10* (2006.01)
- *C08G 12/08* (2006.01)

(52) U.S. Cl.
CPC ........... *B01J 19/002* (2013.01); *B01J 19/26* (2013.01); *C07C 209/78* (2013.01); *C07C 263/10* (2013.01); *C08G 12/08* (2013.01); *B01J 2219/00189* (2013.01); *B01J 2219/00247* (2013.01); *B01J 2219/00765* (2013.01)

(56) References Cited

U.S. PATENT DOCUMENTS

| | | | | |
|---|---|---|---|---|
| 2,402,905 | A * | 6/1946 | Miller | 366/169.1 |
| 2,904,407 | A * | 9/1959 | Rosenthal et al. | 422/133 |
| 3,226,205 | A * | 12/1965 | Rohlfing | 422/134 |
| 5,102,628 | A * | 4/1992 | De Lasa | 422/140 |
| 5,117,048 | A | 5/1992 | Zaby et al. | |
| 5,620,250 | A * | 4/1997 | Chilcoat et al. | 366/168.2 |
| 5,811,259 | A * | 9/1998 | Hall | 435/41 |
| 5,931,579 | A | 8/1999 | Gallus et al. | |
| 6,386,751 | B1 * | 5/2002 | Wootan et al. | 366/170.3 |
| 6,866,831 | B2 * | 3/2005 | Nakao et al. | 422/205 |
| 8,079,752 | B2 * | 12/2011 | Rausch et al. | 366/178.2 |
| 8,162,533 | B2 * | 4/2012 | Hayabusa et al. | 366/175.3 |
| 2005/0047270 | A1 * | 3/2005 | Wood et al. | 366/170.3 |
| 2005/0137417 | A1 | 6/2005 | Meyn et al. | |
| 2008/0118946 | A1 * | 5/2008 | Fabiyi et al. | 435/41 |
| 2008/0159065 | A1 * | 7/2008 | Ding et al. | 366/162.4 |
| 2008/0172934 | A1 | 7/2008 | Firey | |
| 2009/0287033 | A1 * | 11/2009 | Strauss et al. | 585/714 |
| 2010/0137634 | A1 | 6/2010 | Ding et al. | |
| 2010/0160673 | A1 | 6/2010 | Bruns et al. | |
| 2010/0324308 | A1 * | 12/2010 | Hassan et al. | 549/248 |
| 2011/0028573 | A1 * | 2/2011 | Hassan et al. | 518/700 |
| 2011/0075507 | A1 * | 3/2011 | Wootan et al. | 366/124 |

FOREIGN PATENT DOCUMENTS

| | | |
|---|---|---|
| CN | 101811017 | 8/2010 |
| CN | 101811019 | 8/2010 |
| DE | 31 16878 | 11/1982 |
| EP | 0830894 | 3/1998 |
| EP | 2 145 874 | 1/2010 |
| EP | 2 199 277 | 6/2010 |

OTHER PUBLICATIONS

Supplemental European Search Report mailed Aug. 14, 2012, in corresponding European Application No. 10852321.8.

* cited by examiner

HIGH-SPEED MIXING REACTOR AND APPLICATION THEREOF

CROSS-REFERENCE TO RELATED APPLICATIONS

This application is the U.S. national phase application pursuant to 35 U.S.C. §371 of PCT International Patent Application No. PCT/CN2010/080434, filed Dec. 29, 2010. The entire contents of the aforementioned patent application are incorporated herein by this reference.

TECHNICAL FIELD

The present invention relates to a high-speed mixing reactor, and, in particular, to a dynamic reactor capable of rapid mixing fluids so as to effect rapid reaction thereof under a massive capacity of production. Also, the present invention provides a process for the preparation of isocyanates by means of phosgenation by using the reactor and a process of the preparation of polymethylene polyphenylene polyamine from aniline and formaldehyde by using the reactor.

BACKGROUND OF THE INVENTION

In chemical production practices, there are often competing side reactions or reaction chains proceeding rapidly in parallel with the targeted reaction. These reactions, happening among products, intermediates and raw materials, are directly influenced by the reaction progress and the components' concentration distribution in the reaction system. Therefore, the primary mixing of materials is of great importance for the distribution, yield and quality of the targeted products and has strong impact on the designs and energy efficiencies of the overall production processes.

Taking syntheses of isocyanates (e.g., MDI or TDI) for example, the processes are mainly composed of phosgenations at ambient and elevated temperatures. After dissolution of liquid polyamines and liquid phosgene in inert solvents such as chlorobenzene, toluene, dichlorobenzene, chloronaphthalenes, 1,2,4-trichlorobenzenes, etc., the reaction at ambient temperature takes place at 0 to 90° C. and mainly forms amides and polyamine hydrochlorides as well as a small amount of urea. The principal reactions are as follows:

$RNH_2+COCl_2 \rightarrow RNHCOCl+HCl$ (1)

$RNH_2+HCl \rightarrow RNH_2 \cdot HCl$ (2)

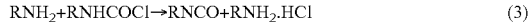

$RNH_2+RNHCOCl \rightarrow RNCO+RNH_2 \cdot HCl$ (3)

$RNH_2+RNCO \rightarrow RNHCONHR$ (4)

At the stage of phosgenation at ambient temperature, polyamines firstly react with phosgene to yield carbamoyl chloride, i.e. Reaction (1), this is a rapid exothermic reaction which proceeds to completion instantaneously; simultaneously, HCl resulting from Reaction (1) reacts with the polyamines rapidly, i.e. Reaction (2), to yield polyamine hydrochloride. Both carbamoyl chloride and polyamine hydrochloride are solids that are insoluble in the reaction system. When the local mixing effect of phosgene and polyamine is relatively poor, excessive polyamines in this area will react with carbamoyl chloride or isocyanate, as shown in Reactions (3) and (4) respectively, yielding urea as an unwanted by-product which is viscous and insoluble in the reaction system. This process exhibits complicated serial competitive reactions. The principal reaction is an instantaneous reaction that completes in milliseconds or even faster, the product of which further reacts with the raw materials rapidly, yielding by-products insoluble in the reaction system. Therefore, the initial mixing of the two raw materials directly decides the yield and selectivity of the target product. To design a high-speed liquid mixing reactor that improves the initial mixing of the two raw material streams, is of great significance for increasing the yield and selectivity of the target product and reducing the viscous by-product.

For another example, the reaction between aniline and formaldehyde to produce polymethylene polyphenylene polyamine, mainly comprises reaction stages including salt-formation, pre-condensation and the rearrangement. In the pre-condensation reaction stage, a liquid mixture of aniline hydrochloride and the circulated liquid is brought into rapid contact with formaldehyde to perform the pre-condensation reaction at a temperature ranging from 20 to 90° C.; a better microscopic dispersion of formaldehyde is beneficial for the results of the reaction. Excessive formaldehyde in local area results in the formation of macromolecular products and more impurities. If formaldehyde is locally over-excessive, there will be web-like polymers generated, which are insoluble and prone to clog up the equipment, and will consequently affect the operation. Therefore, the initial mixing of the two raw materials directly decides the yield and selectivity of the target product. To design a high-speed liquid mixing reactor that improves the initial mixing of the two raw material streams, is of great significance for increasing the yield and selectivity of the target product and reducing the viscous by-product.

The cross-flow mixing is an important technique to achieve rapid mixing of fluids, which can be achieved in one way by jetting one fluid stream via a plurality of apertures into another fluid stream. The jetted stream is split in a plurality of fine steams by the apertures. When jetted into the main stream of the other fluid, each fine stream is rapidly wrapped by the main stream, thereby achieving a rapid mixing of the two streams of fluids.

U.S. Pat. No. 5,117,048 disclosed a hole-jetting reactor (as shown in FIG. 1), which enabled rapid mixing of two streams of fluids by cross flow, jetting one stream (polyamine) into the main stream (phosgene) via apertures evenly distributed over a neck portion. This reactor increased the intensity of turbulence in these two streams of materials mainly by the design of neck portion, so as to improve the initial mixing of the materials. This reactor design allowed reducing the amount of solvent for dilution of the reactants.

U.S. Pat. No. 5,931,579 disclosed a reactor which realized mixing by using a rotator and a stator to engage each other (see FIG. 2). Two fluid streams were fed in between the rotator and the stator and the mixing was driven by the rotation of the rotator. The rotation of the rotator intensified the turbulence and realized the rapid mixing of the two streams of fluids, which reduced the amount of solvent for dilution.

The exemplification above shows that the initial mixing of the two streams of feeds in a well-distributed way is very important. The rapid mixing of streams may be realized to some extent either by using a hole-jetting type reactor which jets a fluid stream into another stream at a high speed or by using a stirring type reactor which feeds two fluid streams into a stirring zone of the rotator. As fluids have thickness, space and turbulence zone are essential to achieve sufficient mix-up. The mixing of two fluids is relatively easier when the fluids have lower flow rates. However, large scale production activities require larger flow channels, which may result in poor distribution and mixing of two streams of feeds in a short time. An extra distance is necessary to achieve the mixing effect but may increase the possibility of side reactions. Both the two types of reactors as discussed above have a capacity limit and a degraded reaction effect under a high workload, and thus it is necessary to develop a high-speed mixing apparatus with better mixing effect to achieve a rapid mixing-reaction of feeds under a massive capacity of production.

SUMMARY OF THE INVENTION

The object of the invention is to provide a novel, high-speed mixing reactor, which enables instantaneously rapid mixing of two streams of feeds under a relatively massive capacity of production, intensifies the main reaction and suppresses the side reactions, so as to improve the yield and quality of the target product(s).

The reactor according to the present invention is designed based on the following concept that a first stream of fluid is introduced through a flow passage, while a second stream of fluid is evenly jetted into the first stream of fluid via an inlet with rotating blade wheel(s). Since the second stream of fluid is introduced into the first stream of fluid via the rotating blade wheel(s), these two streams are therefore evenly dispersed at the very beginning with no need for an extra mixing space. Furthermore, the rotating blade wheel(s) with the feed inlets provide(s) a function of agitation that enables rapid mixing of two streams of feeds with no need for a mixing space. Such a design avoids the scale-up effect since one stream of feed is introduced in dynamic and the inlets may be evenly distributed with respect to the other stream of fluid, eliminating the affection of flow passage space. This enables rapid mixing and reaction of fluids under a massive capacity of production.

The basic structure of the rapid mixing reactor according to the invention is described as follows.

The rapid mixing reactor comprises a first feed-in passage housing, a reactor housing, a second feed-in passage, a hollow blade-wheel feed distributor, a rotation shaft and a first feed distributor; wherein the first feed-in passage housing and the reactor housing are constructed coaxially and connected with each other via the first feed distributor constructed at an end of the first feed-in passage housing; the second feed-in passage, the hollow blade-wheel feed distributor and the rotation shaft are all aligned on the central axis of the reactor; the hollow blade-wheel feed distributor is located within the reactor housing and rotates by the driving of the rotation shaft; the second feed-in passage is connected with a passage inside the hollow blade-wheel feed distributor; the first feed-in passage housing is provided with at least one first feed-in inlet therein; the reactor housing is provided with at least one outlet for the reaction liquid at the distal end; and the first feed distributor and the hollow blade-wheel feed distributor are provided with a first feed-in jetting hole(s) and a second feed-in jetting hole(s), respectively.

In the rapid mixing reactor according to the invention, preferably, the second feed-in passage, the hollow blade-wheel feed distributor, and the rotation shaft are fixed in this sequence along the central axis of the rapid mixing reactor. Further preferably, a dynamic seal ring and a static seal ring that abut closely against each other are placed at the joint where the hollow blade-wheel feed distributor is connected with the second feed-in passage. The dynamic seal ring is placed on the hollow blade-wheel feed distributor and the static seal ring is placed on the end of the second feed-in passage, wherein one side of the static seal ring abuts against the dynamic seal ring on the hollow blade-wheel feed distributor, and the other side is fixed to the first feed distributor via, from inside to outside, a expansion joint and a spring. With this arrangement, the dynamic seal ring and static seal ring can tightly abut against each other while the hollow blade-wheel feed distributor is rotating.

According to another preferred embodiment of the invention, the second feed-in passage is constructed inside the rotation shaft, and is rigidly connected and communicated with the hollow blade-wheel feed distributor, such that the hollow blade-wheel feed distributor is driven to rotate inside the reactor housing by the rotation shaft.

In the rapid mixing reactor according to the invention, preferably, the second feed-in jetting holes are constructed on a lateral face(s) of the hollow blade-wheel feed distributor, or at the outmost edge(s) of the hollow blade-wheel feed distributor, or in a passage(s) extending from the hollow blade-wheel feed distributor perpendicularly to the blade-wheel plate. According to the invention, the second feed-in jetting holes provided in the hollow blade-wheel feed distributor are not particularly limited in term of the shape, size, and number, provided that the process requirements can be met. For example, the shape of the jetting hole (that is, the cross-sectional shape of the passage inside the jetting hole) can be selected from a round, a triangle, a diamond, a trapezoid, a polygon, an ellipse, a square, a rectangle or any combination thereof, preferably a round or a rectangle. The specific size and number of the jetting holes can be determined, according to the specific process requirements and by the person skilled in the art through routine calculation.

In the rapid mixing reactor according to the invention, the first feed distributor is provided with a first feed-in jetting hole(s). Preferably, the first feed-in jetting hole(s) may be ring-like or a plurality of openings evenly distributed. When the first feed-in jetting hole(s) is ring-like, preferably, the ring-like first feed-in jetting hole(s) comprises a plurality of arc-like slits arranged concentrically with the first feed distributor and having the same and/or different inner diameter(s), and in particular, the plurality of arc-like slits having the same inner diameter are in certain distance from each other and concentric with the first feed distributor. With the same principal, the plurality of arc-like slits with different inner diameters are preferably arranged concentrically with the first feed distributor. When the first feed-in jetting hole(s) comprises a plurality of openings evenly distributed, preferably, the shape of the openings may be selected from a round, a triangle, a diamond, a trapezoid, a polygon, an ellipse, a square, a rectangle or any combination thereof, preferably a round. According to the invention, the first feed-in jetting hole(s) is not particularly limited in term of the size and number. The specific size and number of the first feed-in jetting holes can be determined, according to the specific process requirements and by the person skilled in the art through routine calculation.

In the rapid mixing reactor according to the invention, downstream to the hollow blade-wheel feed distributor, preferably, an annular reaction passage regulation block is set up on the inner wall of the reactor housing and projects inwards. This design aims to narrow the flow passage for reactants to a certain extent. The flow rate of reaction liquid can be controlled in a range from 10 m/s to 500 m/s, preferably 30 m/s to 300 m/s by adjusting the distance between the reaction passage regulation block and the rotation shaft. The reaction passage regulation block can be either separately constructed and then attached onto the inner wall of the reactor housing, or alternatively, formed integrally with the reactor housing.

In the rapid mixing reactor according to the invention, preferably, at least one stage of stirring paddle comprising at least two stirring blades are provided perpendicularly on the rotation shaft in order to improve the instantaneously rapid mixing of the streams of reactants downstream the hollow blade-wheel feed distributor. More preferably, there are the first to third stage of stirring paddles perpendicularly provided on the rotation shaft, with each stage of stirring paddle comprising from 2 to 20 stirring blades. Even more preferably, one stage of stirring paddle is perpendicularly provided on the rotation shaft, and the stirring paddle and the reaction passage regulation block are located in the same cross section perpendicular to the central axis of the reactor.

In the rapid mixing reactor according to the invention, more preferably, the inventive reactor further comprises a fitting for a motor disposed at the distal end of the reactor, which would be used to fix the reactor to the motor.

In the rapid mixing reactor according to the invention, the material for the reactor is not particularly limited, and may be those commonly used in the art, comprising, but not limited to, steel, glass, ceramics, alloy, silicon carbide or enamelized steel.

According to the invention, there is also provided a process for the preparation of aliphatic, alicyclic or aromatic isocyanates of general formula (II) from an amine(s) of general formula (I) by using the rapid mixing reactor as described above

$$R(NH_2)_n \qquad (I)$$

$$R(NCO)_n \qquad (II)$$

wherein R denotes an aliphatic, alicyclic or aromatic hydrocarbon radical, and n=1 or ≥2, the process comprising the steps of:

(a) introducing a solution of phosgene into the first feed-in passage of the rapid mixing reactor via the first feed-in inlet and then into the reactor housing by means of the first feed distributor;

(b) introducing an organic solution of the amine of general formula (I) into the reactor housing through the second feed-in passage and by means of the rotating hollow blade-wheel feed distributor; and (c) rapidly mixing and reacting the solution of phosgene introduced via Step (a) and the solution of amine introduced via Step (b) with each other in the reactor housing, and discharging the produced reaction liquid via the reaction liquid outlet.

In the process for preparing isocyanates according to the invention, the solution of phosgene is pure phosgene or a solution of phosgene dissolved in an inert organic solvent at a concentration of 30 to 100 wt %; the organic solution of amine is a dissolution of the amine of general formula (I) in an inert organic solvent at a concentration of 10 to 60 wt %, preferably 20 to 50 wt %.

In the process for preparation of isocyanate according to the invention, the group R in formula (I) and (II) is a $C_2$-$C_{50}$ hydrocarbon radical, an alicyclic $C_2$-$C_{50}$ hydrocarbon radical, or an aromatic $C_6$-$C_{50}$ hydrocarbon radical, preferably, an aliphatic $C_4$-$C_{30}$ hydrocarbon radical, an alicyclic $C_4$-$C_{30}$ hydrocarbon radical, or an aromatic $C_6$-$C_{30}$ hydrocarbon radical, more preferably, an aliphatic $C_5$-$C_{18}$ hydrocarbon radical, an alicyclic $C_5$-$C_{18}$ hydrocarbon radical, or an aromatic $C_6$-$C_{20}$ hydrocarbon radical; n in formula (I) and (II) denotes 2 to 4.

In the process for preparing isocyanates according to the invention, the amine of general formula (I) may be selected from toluene diamine, diphenylmethane-4,4'-diamine, polymethylene polyphenylene polyamine, isophorone diamine, hexane diamine, cyclohexane diamine, naphthalene diamine, p-phenylene diamine, benzene dimethylene diamine, cyclohexane dimethylene diamine, trimethyl-1,6-hexamethylene diamine, tetramethyl m-phenylene dimethylene diamine, dimethyl biphenyl diamine and methyl cyclohexene diamine, preferably, toluene diamine.

In the process for preparing isocyanates according to the invention, the inert solvents for dissolving phosgene or amine may be the same or different. The insert solvent may be independently selected from benzene, toluene, chlorobenzene, o-dichlorobenzene, p-dichlorobenzene, biphenyl chloride, dialkyl terephthalate, diethyl phthalate or any combination thereof.

Besides, the invention provides a process for the preparing polymethylene polyphenylene polyamine (simply referred to as "polyamine") with aniline by using the reactor as described above, comprising the steps of:

(A) introducing a liquid mixture of aniline hydrochloride and a circulated liquid into the first feed-in passage of the rapid mixing reactor via the first feed-in inlet and then into the reactor housing by means of the first feed distributor;

(B) introducing a solution of formaldehyde into the reactor housing through the second feed-in passage and by means of the rotating hollow blade-wheel feed distributor; and (C) subjecting the liquid mixture of aniline hydrochloride and the circulated liquid and the solution of formaldehyde to rapid mixing and pre-condensation in the reactor housing, and then transferring the reaction mixture into a reaction vessel with stirrer to continue with the pre-condensation reaction to obtain a condensation liquid, followed by the steps of heating, molecule rearrangement, neutralization, water washing, refining, etc., to yield the refined polyamine.

Comparing against the prior art, the rapid mixing reactor and the process for the preparing isocyanates by using the reactor described in this invention offer the following advantages:

(1) a stream of feed is evenly distributed into another stream of feed by the rotating distributing passage, thereby realizing the rapid mixing of two streams;

(2) the reactor can be, in principle, scaled up without any limitations, and enables the instantaneously rapid mixing of two streams of liquid under a massive capacity of production, thereby overcoming the drawbacks that both the distance and time for mixing are prolonged because of the enlarged space of flow passages associated with the scale-up of traditional reactors;

(3) the degree of back mixing of the mixed streams is minimized in the mixing reaction zone, and the inventive reactor resembles an ideal "piston flow" reactor; and (4) by using the inventive reactor to provide rapid and homogenous mixing, the side reaction(s) is(are) suppressed to a maximum extent, the amount of the solvent and the excess of phosgene used in the process for the preparation of isocyanates by means of phosgenation can be reduced, the capacity of the facility can be increased, the quality of the product can be improved and the energy consumption can be lowered. In the case that the reactor according to the invention is used for the preparation of polymethylene polyphenylene polyamine from aniline and formaldehyde, the reaction temperature of the pre-condensation can be elevated, the quality of the product can be improved and the facility is enabled with stable operation for long term.

DETAILED DESCRIPTION OF THE PREFERRED EMBODIMENTS OF THE INVENTION

Hereafter a high-speed mixing reactor and a process for the preparation of isocyanates by using the reactor according to the invention will be described in details with reference to the drawings, however, it shall be understood that the present invention is not limited thereto in any way.

Figure 1:
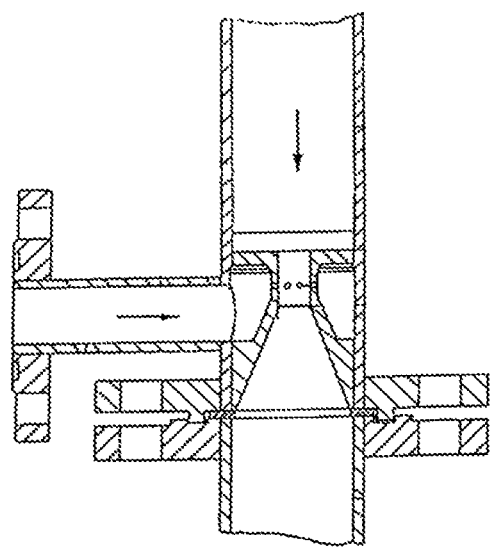
FIG. 1 is a schematic view of the arrangement of a hole-jetting type reactor according to U.S. Pat. No. 5,117,048.
Figure 2:
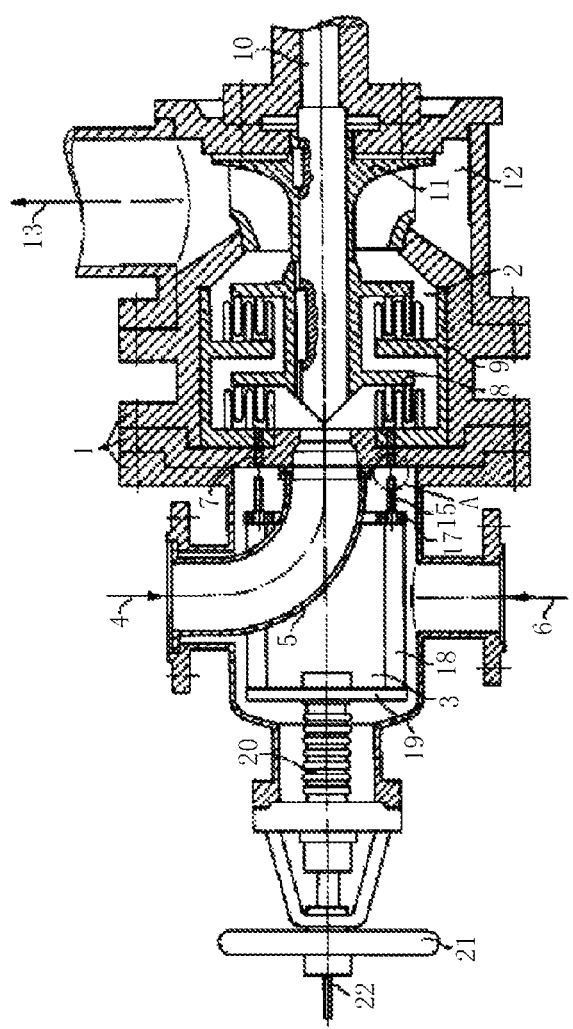
FIG. 2 is a schematic view of the arrangement of a reactor according to U.S. Pat. No. 5,931,579.
Figure 3:
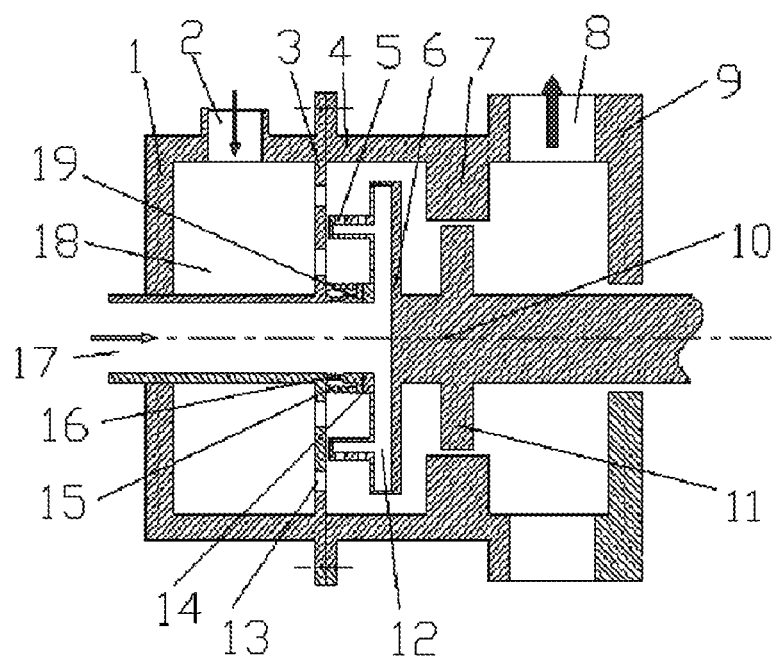
FIG. 3 is a schematic view of the arrangement of a reactor according to a preferred embodiment of the invention.
Figure 5A:
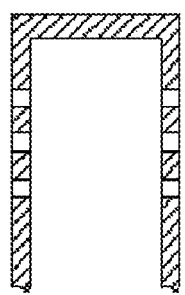
FIG. 5a-5c each are schematic views of the patterns in which the feed-in jetting holes are set up in the hollow blade-wheel feed distributor according to the invention.
Figure 5B:
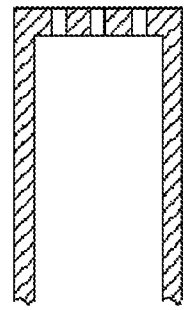
Figure 5C:
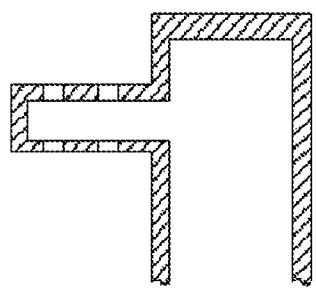

As shown in FIG. 3, the high-speed mixing reactor according to the invention mainly comprises a first feed-in passage housing 1, a reactor housing 4, a second feed-in passage 17, a hollow blade-wheel feed distributor 6, a rotation shaft 10, and a first feed distributor 3. The first feed-in passage housing 1 is constructed coaxially with respect to the reactor housing 4 and communicated with the reaction space inside the reactor housing via the first feed distributor 3 that is set up at the end of the first feed-in passage housing 1. The second feed-in passage 17, the hollow blade-wheel feed distributor 6 and the rotation shaft 10 each are fixed in connection with each other in the sequence along the central axis of the reactor. The hollow blade-wheel feed distributor 6 is located within the reactor housing 4 and rotates axially under the driving force of the rotation shaft 10. The second feed-in passage 17 is connected with the feed passage 12 inside the hollow blade-wheel feed distributor 6. The first feed-in passage housing 1 is set up with at least one first feed-in inlet 2, the first feed-in passage housing 1 and the first feed distributor 3 enclose a space that is defined as the first feed-in passage 18. The distal end of the reactor housing 4 is set up with at least one reaction liquid outlet 8. The first feed distributor 3 is set up with a plurality of first feed-in jetting holes 13 that have proportional distance with each other, and the hollow blade-wheel feed distributor 6 is set up with a plurality of passages perpendicular to its blade-wheel plate. The passages perpendicular to the blade-wheel plate are all set up with a plurality of the second feed-in jetting holes 5. FIG. 5c is a local zoom-in of the passages perpendicular to the blade-wheel plate, which shows a pattern of jetting holes to an extent different from that shown in FIG. 3. Alternatively, the hollow blade-wheel feed distributor 6 according to the invention can be designed with the second feed-in jetting holes as shown in FIG. 5a, 5b or in any other pattern suitable for the invention.

As shown in FIG. 3, the joint between the hollow blade-wheel feed distributor 6 and the second feed-in passage 17 is sealed with a dynamic seal ring 14 and a static seal ring 19 that abut tightly against each other. The dynamic seal ring 14 is placed on the hollow blade-wheel feed distributor 6, and the static seal ring 19 is placed at the end of the second feed-in passage 17. One side of the static seal ring 19 abuts tightly against the dynamic seal ring 14 on the hollow blade-wheel feed distributor 6 and the other side thereof is fixed to the first feed distributor 3 via an expansion joint 16 and a spring 15 positioned outside the expansion joint 16. With this design, the dynamic seal ring 14 on the hollow blade-wheel feed distributor 6 and the static seal ring 19 on the second feed-in passage 17 abut against each other tightly to seal the joint and prevent the leakage of the second feed into the inside of the reactor housing 4 when the rotation shaft 10 works.

Additionally, as shown in FIG. 3, downstream to the hollow blade-wheel feed distributor 6, an annular reaction passage regulation block 7 is fixed on the inner wall of the reactor housing 4 and projects inwards. This design aims to narrow the flow passage of the reaction mixture to a certain extent. The rotation shaft 10 is set up with a Stage-I stirring paddle 11, which is perpendicular to it. The stirring paddle 11 and the reaction passage regulation block 7 are located in the same cross section perpendicular to the central axis of the reactor. More preferably, the reactor described in the invention comprises a motor connection part 9 at the distal end of the reactor, which helps to fix the motor to the reactor.

Figure 6A:
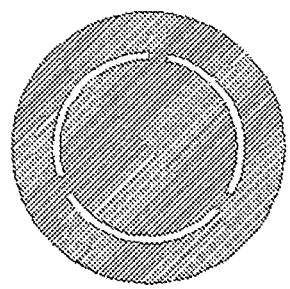
FIG. 6a-6c each are schematic views of the patterns in which the feed-in jetting holes are set up in the first feed distributor according to the invention.
Figure 6B:
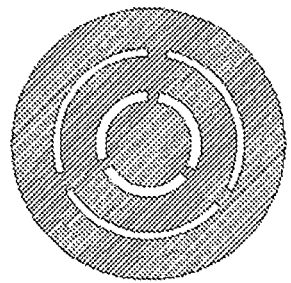
Figure 6C:
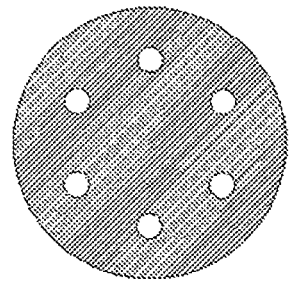

As shown in FIG. 6a-6c, the first feed-in jetting holes 13 set up in the first feed distributor 3 can be ring-like slits or a plurality of openings evenly distributed, provided entrance of the first feed into the reaction zone downstream through the jetting holes 13 is homogeneous.

When the preparation of isocyanates is carried out using the reactor as shown in FIG. 3, at first, a phosgene solution firstly goes through the first feed-in inlet 2 and fills the first feed-in passage 18. Then the phosgene solution enters the reactor housing 4 through the first feed-in jetting holes 13 that are evenly distributed in the first feed distributor 3. At the same time, an organic solution of polyamine corresponding to general formula (I) is introduced through the second feed-in passage 17. The polyamine solution flows through the feed passage 12 inside the rotating hollow blade-wheel feed distributor 6 and is evenly jetted into the stream of the phosgene solution via a plurality of the second feed-in jetting holes 5. Thereby, rapid mixing and reaction can be achieved. The resulting mixture proceeds to downstream under the feeding pressures and enters the next stage reactor via the reaction liquid outlet 8 after being stirred by the stirring paddle 11 perpendicular to the rotation shaft 10. The target isocyanates are formed by temperature elevation in the next stage reactor.

Figure 4:
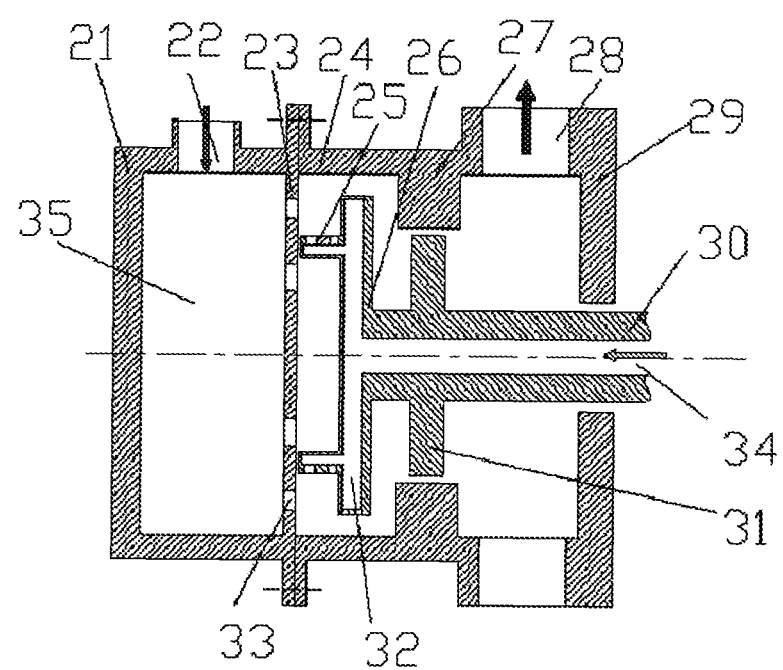
FIG. 4 is a schematic view of the arrangement of a reactor according to another preferred embodiment of the invention.

FIG. 4 is a schematic view of the arrangement of a reactor according to another preferred embodiment of the invention, which shows that the reactor mainly comprises a first feed-in passage housing 21, a reactor housing 24, a second feed-in passage 34, a hollow blade-wheel feed distributor 26, a rotation shaft 30 and a first feed distributor 23. The first feed-in passage housing 21 is constructed coaxially with respect to the reactor housing 24 and communicated with the reaction space inside the reactor housing via the first feed distributor 23 that is set up at an end of the first feed-in passage housing. The second feed-in passage 34 is located inside the rotation shaft 30, and moreover, the second feed-in passage 34, the rotation shaft 30, and the hollow blade-wheel feed distributor 26 are fixed in connection with each other in the sequence along the central axis of the rapid mixing reactor. The hollow blade-wheel feed distributor 26 is fixed to one end of the rotation shaft 30 so that the hollow blade-wheel feed distributor 26 can rotates axially under the driving force of the rotation shaft 30 inside the reactor housing. The second feed-in passage is connected with a feed passage 32 inside the hollow blade-wheel feed distributor 26. The first feed-in passage housing is set up with at least one first feed-in inlet 22 therein, the first feed-in passage housing 21 and the first feed distributor 23 enclose a space that is defined as the first feed-in passage 35. The distal end of the reactor housing is set up with at least one reaction liquid outlet 28. The first feed distributor 23 is set up with a plurality of first feed-in jetting holes 33 that have proportional distance with each other, and the hollow blade-wheel feed distributor 26 is set up with a plurality of passages perpendicular to its blade-wheel plate. The passages perpendicular to the blade-wheel plate are all set up with a plurality of the second feed-in jetting holes 25. Alternatively, the hollow blade-wheel feed distributor according to the invention can be designed with the second feed-in jetting holes arranged as shown in FIG. 5*a*, 5*b* or 5*c* or in any other pattern suitable for the invention.

Additionally, as shown in FIG. 4, downstream to the hollow blade-wheel feed distributor 26, an annular reaction passage regulation block 27 is fixed on the inner wall of the reactor housing and projects inwards. This design aims to narrow the flow passage of the reaction mixtures to a certain extent. The rotation shaft 30 is set up with a Stage-I stirring paddle 31, the stirring paddle 31 and the reaction passage regulation block 27 are located in the same cross section perpendicular to the central axis of the reactor. More preferably, the reactor described in this preferred embodiment comprises a motor connection part 29 at the distal end of the reactor, which helps to fix the reactor to the motor.

Also, when the preparation of isocyanates are carried out using the reactor as shown in FIG. 4, at first, a phosgene solution goes through the first feed-in inlet 22 and fills the first feed-in passage 35. Then the phosgene solution enters the reactor housing through the first feed-in jetting holes 33 that are evenly distributed on the first feed distributor 23. At the same time, an organic solution of polyamine of general formula (I) is introduced through the second feed-in passage 34 inside the rotation shaft. The polyamine solution flows through the feed passage 32 inside the rotating hollow blade-wheel feed distributor 26 and is evenly jetted into the stream of the phosgene solution via a plurality of the second feed-in jetting holes 25. Thereby rapid mixing and reaction can be achieved. The resulting mixtures proceed to downstream under the feeding pressure and enter the next stage reactor via the outlet 28 for the reaction liquid after being stirred by the stirring paddle 31 perpendicular to the rotation shaft 30. The target isocyanates are formed by temperature elevation in the next stage reactor.

Hereafter the rapid mixing reactor according to the invention and the applications thereof will be further illustrated by way of examples, but the invention is not limited thereto in any way.

Example 1

The rapid mixing reactor as shown in FIG. 3 was used for the experiment on MDI production. The first feed distributor of the rapid mixing reactor was designed as shown in FIG. 6*c*. In the first feed distributor a plurality of circular passages with a diameter of 20 mm were evenly distributed. The phosgene solution exited from the circular passages of the first feed distributor at an output rate of 6 m/s. The second feed-in jetting holes having a diameter of 10 mm were set up in the hollow blade-wheel feed distributor in the pattern as shown in FIG. 5*c*. The polyamine solution exited from the second feed-in jetting holes at an output rate of 16 m/s. The rotation shaft rotated at a rotation speed of 1200 rpm. The reactor was employed in an MDI plant for test under a testing load of 220 thousand tons MDI products per year. Chlorobenzene was used as the solvent and the solution of amine in chlorobenzene at a concentration of 33 wt % was fed at a rate of 24 tons per hour. The phosgene solution had a concentration of 80%. The solution of amine in chlorobenzene was jetted into the reactor housing by means of the rotating hollow blade-wheel feed distributor and rapidly reacted with the phosgene solution that entered the reactor housing by means of the first feed distributor. The mass ratio between the two reactants was phosgene: amine=1.7:1. Thereafter, the reaction mixture discharged at the outlet of the reactor was transferred to a cascade of four 40 m$^3$ phosgenators for phosgenation at an elevated temperature until the solution became clear. The temperatures of these four phosgenators in series were 90° C., 105° C., 115° C., and 120° C. respectively. The crude product solution was distilled afterwards to get the polymerized MDI products which had a viscosity of 200 cp and an NCO content of 31.62 wt %.

Example 2

The rapid mixing reactor as shown in FIG. 3 was used for the experiment on MDI production. The first feed distributor of the rapid mixing reactor was designed as shown in FIG. 6*b*. In the first feed distributor a plurality of arc-like slits with different inner diameters and a radial width of 2 mm were evenly distributed. The phosgene solution exited from the arc-like slits at an output rate of 10 m/s. The second feed-in jetting holes having a rectangular hole size of 3 mm×8 mm were set up in the hollow blade-wheel feed distributor in the pattern as shown in FIG. 5*b*. The amine solution exited from the second feed-in jetting holes at an output rate of 22 m/s. The rotation shaft rotates at a rotation speed of 1400 rpm. The reactor was employed in an MDI plant for test under a testing load of 300 thousand tons MDI products per year. Chlorobenzene was used as the solvent and the solution of amine in chlorobenzene at a concentration of 33 wt % was fed at a rate of 33 tons per hour. The phosgene solution had a concentration of 75%. The solution of amine in chlorobenzene was jetted into the reactor housing by means of the second feed distributor and rapidly reacted with the phosgene solution that entered the reactor housing by means of the first feed distributor. The mass ratio between the two reactants was phosgene: amine=1.8:1. Thereafter, the reaction mixture discharged at the outlet of the reactor was transferred to a cascade of four 40 m$^3$ phosgenators for phosgenation at an elevated temperature until the solution became clear. The temperatures of these four phosgenators were 90° C., 105° C., 115° C., and 120° C. respectively. The crude product solution was distilled afterwards to get the polymerized MDI products which had a viscosity of 200 cp and an NCO content of 31.56 wt %.

It can be seen from the two examples described above, that the rapid mixing reactor according to the invention can be used for MDI production with the amine solution at a concentration of as high as 33 wt % and a mass ratio between phosgene and amine as low as 1.7:1, which are far advantageous against the conventional reactors being widely used (with a concentration of the amine solution ranging from 15 to 22% and a mass ratio between phosgene and amine ranging from 2.4 to 4). The reduction of volumes of solvent and phosgene not only improves the efficiency of the reactor and the overall capacity, but also reduces the energy for the condensation the excessive phosgene and the solvent distil-out, bringing a reduction of energy consumption by 40% per kilogram product.

Example 3

The rapid mixing reactor as shown in FIG. 4 was used for the experiment on production of polymethylene polyphenylene polyamine. The first feed distributor of the rapid mixing reactor was designed as shown in FIG. 6*b*. In the first feed distributor a plurality of arc-like slits with different inner diameters and a radial width of 6 mm were evenly distributed. The liquid mixture of aniline hydrochloride and the circulated liquid exited from the arc-like slits at an output rate of 5 m/s.

The second feed-in jetting holes having a rectangular hole size of 3 mm×8 mm were set up in the hollow blade-wheel feed distributor in the pattern as shown in FIG. 5b. The formaldehyde solution exited from the second feed-in jetting holes at an output rate of 20 m/s. The rotation shaft rotates at a rotation speed of 2400 rpm. The reactor was employed in a polymethylene polyphenylene polyamine plant for test under a testing load of 300 thousand tons polyamine per year. The formaldehyde solution (at a concentration of 37 wt %) was fed at a rate of 16 tons per hour. The formaldehyde solution was jetted into the reactor housing by means of the second feed distributor and rapidly reacted with the liquid mixture of aniline hydrochloride and the circulated liquid that entered the reactor housing by means of the first feed distributor. The molar ratio between hydrochloric acid (32 wt %) and the fresh aniline was 0.36:1; the molar ratio between formaldehyde to the fresh aniline was 0.52:1; the total flow rate of the liquid mixture of aniline hydrochloride and the circulated liquid was 220 m³/hour. Thereafter, the reaction mixture discharged at the outlet of the reactor was transferred to a vessel with stirrer to continue with the pre-condensation reaction at a reaction temperature of 65° C., which was followed by the steps of heating, molecule rearrangement, neutralization, water washing, polyamine refining, etc., to collect the refined polymethylene polyphenylene polyamine product with an N-methyl content of 0.12%, which met the specification of the product quality.

The rapid mixing reactor according to the invention enables the pre-condensation reaction temperature to elevate from 40° C. when the reactor of hole-jetting type is used to 65° C. The energy consumption is reduced by 35% and the reactor clean-up once per month due to the clogging has been eliminated as the mixing has been remarkably improved. The operation rate of the whole production facility therefore was significantly increased.

What is claimed is:

1. A rapid mixing reactor, comprising a first feed-in passage housing, a reactor housing, a second feed-in passage, a hollow blade-wheel feed distributor having lateral faces(s), a blade wheel plate, a rotation shaft, and a first feed distributor,
    wherein the first feed-in passage housing is coaxial with respect to the reactor housing and communicates with a reaction space inside the reactor housing via the first feed distributor that is set up at an end of the first feed-in passage housing;
    the second feed-in passage, the hollow blade-wheel feed distributor and the rotation shaft each are fixed in connection with each other in a sequence along the central axis of the reactor; the hollow blade-wheel feed distributor is located within the reactor housing and rotates axially under a driving force of the rotation shaft;
    the second feed-in passage is connected with a feed passage inside the hollow blade-wheel feed distributor;
    the first feed-in passage housing has at least one first feed-in inlet therein;
    the reactor housing has at least one reaction liquid outlet at its distal end; and
    the first feed distributor and the hollow blade-wheel feed distributor are provided with first feed-in jetting hole(s) and second feed-in jetting hole(s), respectively;
    wherein the second feed-in passage, the hollow blade-wheel feed distributor, and the rotation shaft are rigidly coupled in this order along the central axis of the reactor;
    wherein a dynamic seal ring and a static seal ring which can abut tightly against each other are located at the site where the hollow blade-wheel feed distributor is connected with the second feed-in passage; and
    the dynamic seal ring is located on the hollow blade-wheel feed distributor, and the static seal ring is located at the end of the second feed-in passage, wherein one side of the static seal ring abuts against the dynamic seal ring on the hollow blade-wheel feed distributor, and the other side of the static seal ring is fixed to the first feed distributor via, from inside to outside, an expansion joint and a spring.

2. The reactor according to claim 1, wherein the second food in passage is constructed inside the rotation shaft, and is rigidly connected and communicated with the hollow blade-wheel feed distributor.

3. The reactor according to claim 1, wherein the reactor further comprises a fitting for a motor placed at the distal end of the reactor.

4. A process for the preparation of polymethylene polyphenylene polyamines from aniline with the reactor according to claim 1, comprising the steps of:
    (A) introducing a liquid mixture of aniline hydrochloride and a stream of circulated reaction liquid into the first feed-in passage of the rapid mixing reactor via the first feed-in inlet and then into the reactor housing by means of the first feed distributor;
    (B) introducing a solution of formaldehyde into the reactor housing through the second feed-in passage and via the rotating hollow blade-wheel feed distributor; and
    (C) subjecting the liquid mixture of aniline hydrochloride and the circulated reaction liquid and the solution of formaldehyde to rapid mixing and pre-condensation in the reactor housing, and then transferring the reaction liquid into a reaction vessel with agitation to proceed with the pre-condensation to obtain a condensation liquid, followed by the steps of heating, molecule rearrangement, neutralization, water washing and refining to yield the refined polymethylene polyphenylene polyamine.

5. The reactor according to claim 1, wherein the first feed-in jetting holes are annulus-like or a plurality of openings evenly distributed;
    when the first feed-in jetting holes are annulus-like, the annulus-like first feed-in jetting holes comprise a plurality of arc-like slits arranged concentrically with the first feed distributor and have the same and/or different inner diameter(s), with the plurality of arc-like slits being spaced away from each other; and
    when the first feed-in jetting holes comprise a plurality of openings evenly distributed, the openings have a shape selected from a round, a triangle, a diamond, a trapezoid, a polygon, an ellipse, a square, a rectangle or any combination thereof.

6. The reactor according to claim 5, wherein the first feed-in jetting holes comprise a plurality of openings evenly distributed, and the openings are round.

7. The reactor according to claim 1, wherein the second feed-in jetting holes are constructed on the lateral face(s) or at the outmost edge(s) of the hollow blade-wheel feed distributor, or in a passage(s) extending from the hollow blade-wheel feed distributor perpendicularly to the blade-wheel plate.

8. The reactor according to claim 7, wherein the second feed-in jetting holes in the hollow blade-wheel feed distributor have a shape selected from a round, a triangle, a diamond, a trapezoid, a polygon, an ellipse, a square, a rectangle or any combination thereof.

9. The reactor according to claim 8, wherein the second feed-in jetting holes in the hollow blade-wheel feed distributor are round or rectangular.

10. The reactor according to claim 1, wherein an annular reaction passage regulation block is fixed on the inner wall of the reactor housing and projects inward, downstream to the hollow blade-wheel feed distributor.

11. The reactor according to claim 10, wherein at least one stirring paddle comprising at least two stirring blades is fixed on the rotation shaft and perpendicularly to it.

12. The reactor according to claim 11, wherein the stirring paddle is perpendicularly fixed on the rotation shaft, and the stirring paddle and the reaction passage regulation block are located in the same cross section perpendicular to the central axis of the reactor.

13. A process for the preparation of aliphatic, alicyclic or aromatic isocyanates of general formula (II) from an amine(s) of general formula (I) by using the reactor according to claim 1, $$R(NH_2)_n \quad (I)$$

$$R(NCO)_n \quad (II)$$

wherein R denotes aliphatic, alicyclic or aromatic hydrocarbon radicals, and n=1 or ≥2, the process comprising the steps of:
(a) introducing a solution of phosgene into the first feed-in passage of the rapid mixing reactor via the first feed-in inlet and then into the reactor housing by means of the first feed distributor;
(b) introducing an organic solution of the amine(s) of general formula (I) into the reactor housing through the second feed-in passage and via the rotating hollow blade-wheel feed distributor; and
(c) rapidly mixing and reacting the solution of phosgene introduced via step (a) and the solution of amine(s) introduced via step (b) with each other in the reactor housing, and discharging the produced reaction liquid via the outlet for reaction liquid.

14. The process according to claim 13, wherein the solution of phosgene comprises pure phosgene or a solution of phosgene in an inert organic solvent at a concentration of 30 to 100 wt %.

15. The process according to claim 13, wherein the organic solution of amine(s) comprises the amine(s) of general formula (I) in an inert organic solvent at a concentration of 10 to 60 wt %.

16. The process according to claim 13, wherein the amine of general formula (I) is selected from the group consisting of toluene diamine, diphenylmethane-4,4'-diamine, polymethylene polyphenylene polyamine, isophorone diamine, hexane diamine, cyclohexane diamine, naphthalene diamine, p-phenylene diamine, benzene dimethylene diamine, cyclohexane dimethylene diamine, trimethyl-1,6-hexamethylene diamine, tetramethyl m-phenylene dimethylene diamine, dimethyl biphenyl diamine and methyl cyclohexene diamine.

17. The process according to claim 13, wherein the solvents for dissolving phosgene or amine are inert solvents and may be the same or different, and are independently selected from the group consisting of benzene, toluene, chlorobenzene, o-dichlorobenzene, p-dichlorobenzene, biphenyl chloride, dialkyl terephthalate, diethyl phthalate or any combination thereof.

18. The process according to claim 13, wherein the group R in formula (I) and (II) is an aliphatic C2-C50 hydrocarbon radical, an alicyclic C2-C50 hydrocarbon radical, or an aromatic C6-C50 hydrocarbon radical; and n in formula (I) and (II) denotes 2 to 4.

19. The process according to claim 18, wherein the group R in formula (I) and (II) is an aliphatic C4-C30 hydrocarbon radical, an alicyclic C4-C30 hydrocarbon radical, or an aromatic C6-C30 hydrocarbon radical; and n in formula (I) and (II) denotes 2 to 4.

20. The process according to claim 18, wherein the group R in formula (I) and (II) is an aliphatic C5-C18 hydrocarbon radical, an alicyclic C5-C18 hydrocarbon radical, or an aromatic C6-C20 hydrocarbon radical; and n in formula (I) and (II) denotes 2 to 4.

* * * * *